(12) United States Patent  
Marquais-Bienewald et al.

(10) Patent No.: US 8,097,045 B2
(45) Date of Patent: Jan. 17, 2012

(54) POLYMERIC HAIR DYES

(75) Inventors: Sophie Marquais-Bienewald, Hegenheim (FR); Christian Cremer, Lörrach (DE); Olof Wallquist, Bottmingen (CH); Beate Fröhling, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/812,778

(22) PCT Filed: Jan. 7, 2009

(86) PCT No.: PCT/EP2009/050098
§ 371 (c)(1),
(2), (4) Date: Jan. 13, 2011

(87) PCT Pub. No.: WO2009/090125
PCT Pub. Date: Jul. 23, 2009

(65) Prior Publication Data
US 2011/0107525 A1    May 12, 2011

(30) Foreign Application Priority Data

Jan. 17, 2008 (EP) .................. 08150363

(51) Int. Cl.
*A61Q 5/10* (2006.01)
*C07D 213/22* (2006.01)

(52) U.S. Cl. ............. 8/405; 8/552; 8/554; 8/647; 8/657; 546/264

(58) Field of Classification Search ............. 8/405, 552, 8/647, 657; 546/264
See application file for complete search history.

(56) References Cited

U.S. PATENT DOCUMENTS

| | | | |
|---|---|---|---|
| 3,567,678 A | 3/1971 | Kalopissis | |
| 4,911,731 A * | 3/1990 | Loveless et al. | ........... 8/405 |
| 5,891,199 A | 4/1999 | Wachter | |
| 6,281,315 B1 | 8/2001 | Gonzalez et al. | |
| 6,306,182 B1 | 10/2001 | Chan | |
| 7,731,761 B2 | 6/2010 | Marquais-Bienewald | |

FOREIGN PATENT DOCUMENTS

| | | |
|---|---|---|
| DE | 1492063 A1 | 10/1969 |
| DE | 19510312 A1 | 9/1996 |
| WO | 95/01772 A | 1/1995 |
| WO | 97/04510 A | 2/1997 |
| WO | 98/02492 A | 1/1998 |
| WO | 01/17356 A | 3/2001 |
| WO | 2006/134051 A | 12/2006 |
| WO | 2008/009579 A | 1/2008 |

OTHER PUBLICATIONS

Copending U.S. Appl. No. 12/812,781, filed Jul. 14, 2010.
Copending U.S. Appl. No. 12/812,785, filed Jul. 14, 2010.
Copending U.S. Appl. No. 12/812,782, filed Jul. 14, 2010.

* cited by examiner

Primary Examiner — Eisa Elhilo
(74) Attorney, Agent, or Firm — Shiela A. Loggins

(57) ABSTRACT

Disclosed are olymeric dye of formula (1a), (1b), (1c), A and B, independently from each other represent a polymer backbone; $X_1$ and $X_2$ independently from each other are a linkage group selected from $—C_1-C_{30}$alkylene- or $—C_2-C_{12}$alkenylene-, which is interrupted and/or terminated at one or both ends by one or more than one $—S—$, $—N—$, $—N=$, $—N(R_5)—$, $—S(O)—$, $—SO_2—$, $—(CH_2CH_2O)_{1-5}—$, $—(CH_2CH_2CH_2—O)_{1-5}—$, $—C(O)—$, $—C(O)O—$, $—OCO—$, (II), $—CON(R_1)—$, $—C(NR_1R_2)_2—$, $—(R_1)NC(O)—$, $—C(S)R_1—$; or an optionally substituted, saturated or unsaturated, fused or non-fused aromatic or non-aromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1-C_{30}$alkyl, $C_1-C_{30}$alkoxy, $C_2-C_{12}$alkenyl, $C_5-C_{10}$aryl, $C_5-C_{10}$cycloalkyl, $C_1-C_{10}$alkyl($C_5-C_{10}$arylene), hydroxy or halogen; $R_1$ and $R_2$ independently from each other are hydrogen; unsubstituted or substituted, straight-chain or branched, monocyclic or polycyclic, interrupted or uninterrupted $C_1-C_{14}$alkyl; $C_2-C_{14}$alkenyl; $C_6-C_{10}$aryl; $C_6-C_{10}$aryl-$C_1-C_{10}$alkyl; or $C_5-C_{10}$alkyl($C_5-C_{10}$aryl); $Y_1$ and $Y_2$ independently from each other are a residue of an organic dye; or hydrogen; wherein at least one of $Y_1$ and $Y_2$ is a residue of an organic dye; $An_1$, $An_2$ and $An_3$, independently from each other are an anion; a and b independently from each other are a number from 1 to 3; m is a number from 0 to 5000; n is a number from 0 to 5000; and p is a number from 1 to 5000; wherein the sum of $m+n+p \geq 3$. The dyes are distinguished by their depth of shade and their good fastness properties to washing, such as, for example, fastness to light, shampooing and rubbing.

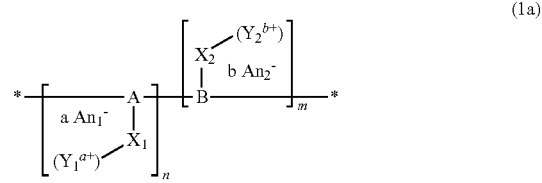

(1a)

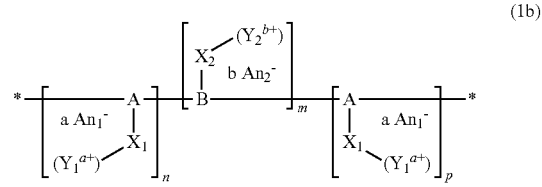

(1b)

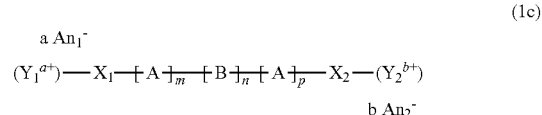

(1c)

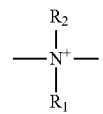

(II)

20 Claims, No Drawings

POLYMERIC HAIR DYES

The present invention relates to novel polymeric dyes and compositions comprising these compounds, to a process for their preparation and to their use for dyeing of organic materials, such as keratin-containing fibers, wool, leather, silk, cellulose or polyamides.

It is well known that cationic compounds have a good affinity to negative charged hair. These characteristics have been used to contact the hair with small molecules, but also with polymers.

Numerous cationic polymeric dyes have been disclosed for use as a colorant for human hair, for example in U.S. Pat. Nos. 4,228,259, 4,182,612 or FR 2 456 764. These references teach that the polymer moiety has the cationic charge.

Surprisingly it was found that very good dyeing results are obtained with polymeric hair dyes wherein the cationic charge is located in dye moiety.

Therefore the present invention relates to polymeric dyes of formula (1a)

$$* \left[ \begin{array}{c} aAn_1^- \\ (Y_1^{a+}) \diagdown X_1 \end{array} \middle| A \middle| \begin{array}{c} X_2 \diagup (Y_2^{b+}) \\ | \quad bAn_2^- \\ B \end{array} \right]_n *; \quad (1a)$$

$$* \left[ \begin{array}{c} aAn_1^- \\ (Y_1^{a+}) \diagdown X_1 \end{array} \middle| A \middle| \begin{array}{c} X_2 \diagup (Y_2^{b+}) \\ | \quad bAn_2^- \\ B \end{array} \right]_n \left[ \begin{array}{c} A \\ | \\ X_1 \diagdown (Y_1^{a+}) \\ aAn_1^- \end{array} \right]_p *; \text{ or } \quad (1b)$$

$$aAn_1^- \\ (Y_1^{a+}) - X_1 + A \mathbin{\Huge]}_m + B \mathbin{\Huge]}_n + A \mathbin{\Huge]}_p - X_2 - (Y_2^{b+}); \\ bAn_2^- \quad (1c)$$

wherein

A and B, independently from each other represent a polymer backbone;

$X_1$ and $X_2$ independently from each other are a linkage group selected from —$C_1$-$C_{30}$alkylene- or —$C_2$-$C_{12}$alkenylene-, which is interrupted and/or terminated at one or both ends by one or more than one —S—, —N—, —N=, —N($R_5$)—, —S(O)—, —$SO_2$—, —($CH_2CH_2$—O)$_{1-5}$—, —($CH_2CH_2CH_2$—O)$_{1-5}$—, —C(O)—, —C(O)O—, —OCO—, $$\begin{array}{c} R_2 \\ | \\ -N^+- , \\ | \\ R_1 \end{array}$$

—CON($R_1$)—, —C($NR_1R_2$)$_2$—, —($R_1$)NC(O)—, —C(S)$R_1$—; or an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or halogen;

$R_1$ and $R_2$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

$Y_1$ and $Y_2$ independently from each other are a residue of an organic dye; or hydrogen;

wherein at least one of $Y_1$ and $Y_2$ is a residue of an organic dye;

$An_1$, $An_2$ and $An_3$, independently from each other are an anion;

a and b independently from each other are a number from 1 to 3;

m is a number from 0 to 5000;

n is a number from 0 to 5000; and p is a number from 1 to 5000;

wherein the sum of m+n+p≧3.

$C_1$-$C_{14}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecyl, dodecyl, tredecyl or tetradecyl.

$C_2$-$C_{14}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_6$-$C_{10}$aryl is for example phenyl or naphthyl.

$C_1$-$C_{30}$alkylene is for example methylene, ethylene, propylene, isopropylene, n-tetramethylene, sec-tetramethylene, tert-tetramethylene, n-pentamethylene, 2-pentamethylene 3-pentamethylene, 2,2'-dimethylpropylene, cyclopentamethylene, cyclohexamethylene, n-hexamethylene, n-octamethylene, 1,1',3,3'-tetramethyltetramethylene, 2-ethylhexamethylene, nonamethylene, decamethylene, tridecamethylene, tetradecamethylene, pentadecamethylene, hexadecamethylene, heptadecamethylene, octadecamethylene, nonadecamethylene or eicosamethylene.

In formulae (1a), (1b) and (1c) preferably $X_1$ and $X_2$ independently from each other are a bivalent radical of formula $$-(T)_t(Z)-, \text{ wherein} \quad (1a)$$

T is —$C_1$-$C_{12}$alkylene; —$C_2$-$C_{12}$alkenylene-; —C(O)—; —($CH_2CH_2$—O)$_{1-5}$—; —($CH_2CH_2CH_2$—O)$_{1-5}$—; —C(O)O—; —OC(O)—; —N($R_1$)—; —CON($R_1$)—; —($R_1$)NC(O)—; —O—; —S—; —S(O)—; —S(O)$_2$—; —S(O)$_2$N($R_1$)—; or —$N^+$($R_1$)($R_2$)—;

Z is a biradical of formula (1d)

$$\begin{array}{c} * \diagdown \diagup N \diagdown \diagup * \\ | \quad \quad | \\ N \diagdown \diagup N \\ | \\ Y \end{array} \quad (1d)$$

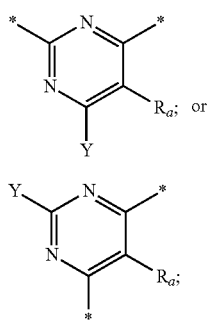

$R_1$ and $R_2$ independently from each other are hydrogen; $C_1$-$C_6$alkyl; $C_1$-$C_6$alkoxy; $C_1$-$C_6$-alkylamino; $C_6$-$C_{10}$aryloxy; or $C_6$-$C_{10}$arylamino;

$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; $SO_2R_5$; chlorine; or fluorine;

Y is $R_a$; $Y_1^{a+}$; or $Y_2^{b+}$; wherein $Y_1$ and $Y_2$ are defined as in claim 1;

a and b independently from each other are 1, 2 or 3; and t is 0 or 1.

In formulae (1a), (1b) and (1c) preferably $Y_1$ and $Y_2$ independently from each other are selected from the group of anthraquinone, acridine, azo, azamethine, hydrazomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, quinoneimine, quinacridone, quinophtalone, styryl, stilbene, xanthene, thiazine and thioxanthene dyes.

More preferably, $Y_1$ and $Y_2$ independently from each other are selected from azo, azomethine, hydrazomethine, anthraquinone, merocyanine, methine and styryl dyes.

Most preferably $Y_1$ and $Y_2$ have the same meaning.

Preferably in formulae (1a), (1b) and (1c)

A and B, independently from each other are selected from polymers of monoolefins and diolefins; mixtures of polymers of monoolefins and diolefins; copolymers of monoolefins and diolefins with each other or with other vinyl monomers; polystyrene, poly(p-methylstyrene), poly(α-methylstyrene); aromatic homopolymers and copolymers derived from vinyl aromatic monomers; copolymers and hydrogenated copolymers of vinyl aromatic monomers and comonomers selected from ethylene, propylene, dienes, nitriles, acids, maleic anhydrides, maleimides, vinyl acetate and vinyl chloride or acrylic derivatives and mixtures thereof; graft copolymers of vinyl aromatic monomers; halogen-containing polymers; polymers derived from α,β-unsaturated acids and derivatives thereof; copolymers derived from α,β-unsaturated acids and derivatives thereof with other unsaturated monomers; polymers derived from unsaturated alcohols and amines or the acyl derivatives or acetals thereof; homopolymers and copolymers of cyclic ethers; polyacetals; polyphenylene oxides and sulfides, and mixtures of polyphenylene oxides with styrene polymers or polyamides; Polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; polyguanidines, polyureas, polyimides, polyamide-imides, polyetherimids, polyesterimids, polyhydantoins and polybenzimidazoles; polyesters derived from dicarboxylic acids and diols and/or from hydroxycarboxylic acids or the corresponding lactones; polycarbonates and polyester carbonates; polyketones; polysulfones, polyether sulfones and polyether ketones; Crosslinked polymers derived from aldehydes on the one hand and phenols, ureas and melamines on the other hand; polysiloxanes; natural polymers; and blends of the mentioned polymers.

Examples for polymers of monoolefins and diolefins are polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

Mixtures of the polymers mentioned above are for example mixtures of polypropylene with polyisobutylene, polypropylene with polyethylene (for example PP/HDPE, PP/LDPE) and mixtures of different types of polyethylene (for example LDPE/HDPE).

Examples of copolymers of monoolefins and diolefins with each other or with other vinyl monomers are ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

Homopolymers and copolymers mentioned above may have any stereostructure including syndiotactic, isotactic, hemi-isotactic or atactic; where atactic polymers are preferred. Stereoblock polymers are also included.

Examples of aromatic homopolymers and copolymers derived from vinyl aromatic monomers including styrene are α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

Examples for copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof are for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

Hydrogenated aromatic polymers derived from hydrogenation of polymers mentioned above especially including polycyclohexylethylene (PCHE) prepared by hydrogenating atactic polystyrene, often referred to as polyvinylcyclohexane (PVCH).

Homopolymers and copolymers may have any stereostructure including syndiotactic, isotactic, hemi-isotactic or atactic; where atactic polymers are preferred. Stereoblock polymers are also included.

Examples for graft copolymers of vinyl aromatic monomers are styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

Examples for halogen-containing polymers are polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

Examples for polymers derived from α,β-unsaturated acids and derivatives thereof are polyacrylates and polymethacrylates; polymethyl methacrylates, polyacrylamides and polyacrylonitriles, impact-modified with butyl acrylate.

Examples for copolymers of the monomers mentioned above with each other or with other unsaturated monomers are acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

Examples for polymers derived from unsaturated alcohols and amines or the acyl derivatives or acetals thereof are for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in above.

Examples for homopolymers and copolymers of cyclic ethers are polyalkylene glycols, polyethylene oxide, polypropylene oxide or copolymers thereof with bisglycidyl ethers.

Examples for polyacetals are polyoxymethylene and those polyoxymethylenes which contain ethylene oxide as a comonomer; polyacetals modified with thermoplastic polyurethanes, acrylates or MBS.

Examples for polyamides and copolyamides derived from diamines and dicarboxylic acids and/or from aminocarboxylic acids or the corresponding lactams are polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

Examples for polyesters derived from dicarboxylic acids and diols and/or from hydroxycarboxylic acids or the corresponding lactones are polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

Examples for crosslinked polymers derived from aldehydes on the one hand and phenols, ureas and melamines on the other hand are phenol/formaldehyde resins, urea/formaldehyde resins and melamine/formaldehyde resins.

Examples for natural polymers are cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

Example for blends of the aforementioned polymers (polyblends) are PP/EPDM, Polyamide/EPDM or ABS, PVC/

EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Preferably both the polymer backbone (A and B) and residue of an organic dye ($Y_1$ and $Y_2$) have a functional group selected from the electophilic group selected from halide, tosylate, mesylate, methoxy, acid chloride, sulfonyl chloride, epoxides, anhydride; or a nucleophilic group selected from amine, hydroxyl and thiol.

Preferably the molecular weight of the polymeric dye is from 400 to 50000.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formate, acetate, propionate or a complex anion, such as the zinc chloride double salt.

Most preferably are polymeric dyes of formula

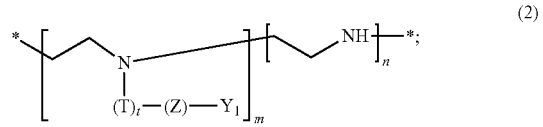

(2)

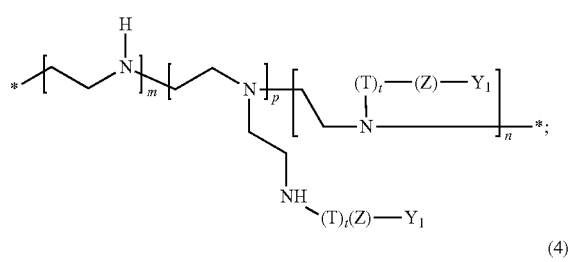

(3)

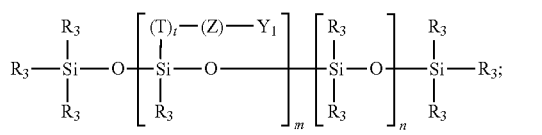

(4)

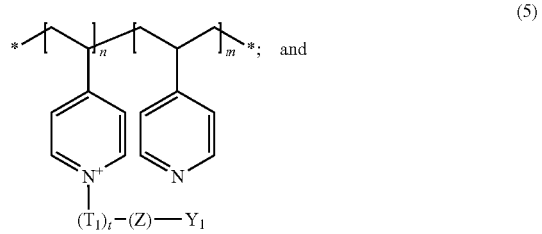

(5) and

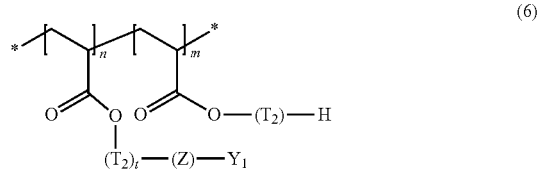

(6)

T, $T_1$ and $T_2$, independently from each other —$C_1$-$C_{12}$alkylene; —$C_2$-$C_{12}$alkenylene-; —C(O)—; —(CH$_2$CH$_2$—O)$_{1-5}$—; —(CH$_2$CH$_2$CH$_2$—O)$_{1-5}$—; —C(O)O—; —OC(O)—; —N($R_1$)—; —CON($R_1$)—; —($R_1$)NC(O)—; —O—; —S—; —S(O)—; —S(O)$_2$—; —S(O)$_2$N($R_1$)—; or —N$^+$($R_1$)($R_2$)—;

Z, $Y_1$ and t are defined as in formula (2); and m, n and p as in formulas (1a), (1b) or (1c).

The dyes of formula (1a), (1b) or (1c) according to the present invention are suitable for dyeing organic materials, such as keratin-containing fibers, wool, leather, silk, cellulose or polyamides, cotton or nylon, and preferably human hair including body hairs like eyebrows, eyelashes, pubic-, breast-, armpit- and beard hair. Also animal hair can be colored with the inventive hair dyes.

The dyeings obtained are distinguished by their depth of shade and their good fastness properties to washing, such as, for example, fastness to light, shampooing and rubbing.

Generally, hair dyeing agents on a synthetic base may be classified into three groups:
temporary dyeing agents
semipermanent dyeing agents, and
permanent dyeing agents.

The multiplicity of shades of the dyes can be increased by combination with other dyes.

Therefore the dyes of formula (1a), (1b) and (1c) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of formula (1a), (1b) and (1c) may be used in combination with at least one single direct dye different from the dyes of formula (1a), (1b) and (1c).

The inventive polymeric hair dyes do not require any addition of an oxidizing agent to develop their dyeing effect. This fact could possibly reduce the damage of the hair. In addition many of the perceived or documented disadvantages of current oxidative hair dyes like their skin irritation, skin sensibilization and allergenic properties can be prevented by the use of the inventive hair dyes. Also, the inventive hair dyes are easier to apply and to use in formulations than oxidative hair dyes since no chemical reaction occurs upon application on the head. Especially advantageous is the fact, that the dyeing time is significantly shorter (ca. 5-10 min) than dyeing using oxidative dyes.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

Furthermore, the dyes of formula (1a), (1b) and (1c) may be combined with at least one cationic azo dye, for example the compounds disclosed in GB-A-2 319 776 as well as the oxazine dyes described in DE-A-299 12 327 and mixtures thereof with the other direct dyes mentioned therein.

The dyes of formula (1a), (1b) and (1c) may also be combined with acid dyes, for example the dyes which are known from the international names (Color index), or trade names.

The dyes of formula (1a), (1b) and (1c) may also be combined with uncharged dyes.

Furthermore, the dyes of formula (1a), (1b) and (1c) may also be used in combination with oxidation dye systems.

Furthermore, autooxidizable compounds may be used in combination with the dyes of formula (1a), (1b) and (1c).

The dyes of formula (1a), (1b) and (1c) may also be used in combination with naturally occurring dyes.

Furthermore, the dyes of formula (1a), (1b) and (1c) may also be used in combination with capped diazotised compounds.

Suitable diazotised compounds are for example the compounds of formulae (1)-(4) in WO 2004/019897 (bridging gages 1 and 2) and the corresponding watersoluble coupling components (I)-(IV) as disclosed in the same reference on p. 3 to 5.

Furthermore, the dyes of the present invention can also be combined with dyes which are prepared by the reaction of a reactive carbonyl-compound and a CH-acidic compound as described in DE 10 2006 062 435 A1, WO 00038638, DE 10241076 and WO 05120445;
- with thiadiazol dyes as described in DE 10 2006 036898 and DE 10 2005 055496,
- with fluorescent stilbenic sulphur dyes as described in for example WO 07110532, WO 07110542,
- with tetraazapentamethine dyes as described in WO 07071684 and WO 07071686,
- with dimeric cationic dyes as described in FR 2879195, FR 2879127, FR 2879190, FR 2879196, FR 2879197, FR 2879198, FR 2879199, FR 2879200, FR 2879928, FR 2879929, WO 06063869,
- with azo and styryl dyes as described in EP 0850636,
- with polymeric anionic dyes as described in FR 2882929,
- with disulfide dyes as described in WO 0597051, EP 1647580, WO 06136617,
- with thiol dyes as described in WO 07025889, WO 07039527, and
- with conductive polymers as described in US 20050050650, U.S. Pat. No. 7,217,295

The present invention also relates to formulations, which are used for the dyeing of organic materials, preferably keratin-containing fibers, and most preferably human hair, comprising at least one dye of formula (1a), (1b) and (1c).

Preferably the dyes of formula (1a), (1b) and (1c) are incorporated into the composition for treating organic material, preferably for dyeing in amounts of 0.001-5% by weight (hereinafter indicated merely by "%"), particularly 0.005-4%, more particularly 0.1-3%, based on the total weight of the composition.

The dyeing compositions of the present invention are applied on the hair in a temperature range of 10 to 200, preferably 18 to 80, and most preferably from 20 to 40° C.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, I. 16 to 31.

The pH value of the ready-to-use dyeing compositions is usually from 2 to 11, preferably from 5 to 10.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, I. 70 to col 3, I. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations of from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, I. 1 to p. 244, I. 12.

If the dyes of formula (1a), (1b) and (1c) are used together with oxidation dyes and/or the addition salts thereof with an acid, they may be stored separately or together. Preferably the oxidation dyes and the direct dyes which are not stable to reduction or base are stored separately.

The dyes of formula (1a), (1b) and (1c) may be stored in a liquid to paste-like preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuavents are preferably used in the hair dyeing compositions of the present invention: -non-ionic polymers, -cationic polymers, acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers; -quaternised polyvinyl alcohol, zwitterionic and amphoteric polymers, anionic polymers, thickeners, structuring agents, hair-conditioning compounds, protein hydrolysates, perfume oils, dimethyl isosorbitol and cyclodextrins, solubilisers, anti-dandruff active ingredients, substances for adjusting the pH value, panthenol, pantothenic acid, allantoin, pyrrolidone carboxylic acids and salts thereof, plant extracts and vitamins, cholesterol; -light stabilisers and UV absorbers, consistency regulators, fats and waxes, fatty alkanolamides, polyethylene glycols and polypropylene glycols having a molecular weight of from 150 to 50 000, complexing agents, swelling and penetration substances, opacifiers, pearlising agents, propellants, antioxidants, sugar-containing polymers, quaternary ammonium salts and bacteria inhibiting agents.

The dyeing compositions according to the present invention generally comprise at least one surfactant. Suitable surfactants are zwitterionic or ampholytic, or more preferably anionic, non-ionic and/or cationic surfactants.

A further embodiment of the present invention relates to the dyeing of keratin-containing fibers.

The processes comprises
(a) treating the keratin-containing fiber with at least one dye of formula (1a), (1b) and (1c) and
(b) leaving the fiber to stand and then rinsing the fiber.

The dyes of formula (1a), (1b) and (1c) are suitable for all-over dyeing of the hair, that is to say when dyeing the hair on a first occasion, and also for re-dyeing subsequently, or dyeing of locks or parts of the hair.

The dyes of formula (1a), (1b) and (1c) are applied on the hair for example by massage with the hand, a comb, a brush, or a bottle which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of formula (1a), (1b) and (1c), a base and an oxidizing agent.

A preferred embodiment for dyeing keratin-containing fibers, in particular human hair, with a dye of formula (1a), (1b) and (1c) and an oxidizing agent, comprises
$a_1$) treating the keratin-containing fiber with the oxidizing agent, which optionally contains at least one dye of formula (1a), (1b) and (1c),
$b_1$) treating the keratin-containing fiber with an oxidizing agent free composition, which optionally contains at least one dye of formula (1a), (1b) and (1c); or alternatively
$a_2$) treating the keratin-containing fiber with an oxidizing agent free composition, which optionally contains at least one dye of formula (1a), (1b) and (1c);
$b_2$) treating the keratin-containing fiber with an oxidizing agent, which optionally contains least one dye of formula (1a), (1b) and (1c),
with the proviso that at least in one of the process steps $a_1$), $a_2$), $b_1$) or $b_2$) a dye of formula (1a), (1b) and (1c) is present.

In general, the oxidizing agent containing composition is left on the fiber for 0 to 45 minutes, in particular for 15 to 30 minutes at 15 to 45° C.

The oxidizing agent free composition usually comprises customary adjuvants and additives. Preferred are those, which are described in German Patent Application, in col 3, I. 17 to I. 41.

In general, the dye of formula (1a), (1b) and (1c) and the oxidizing agent free composition are left on the fiber for 5 to 45 minutes, in particular for 10 to 25 minutes at 15 to 50° C.

One preferred embodiment of the process is to wash the hair after dyeing with a shampoo and/or a weak acid, such as citric acid or tartrate acid.

The dyes of formula (1a), (1b) and (1c) which are stable to reduction can be stored together with the oxidizing agent free compositions and may be applied as a single composition.

Advantageously the compositions comprising a dye of formula (1a), (1b) and (1c) which are not stable to reduction are prepared with the oxidizing agent free composition just before the dyeing process.

In a further embodiment, the dye of formula (1a), (1b) and (1c) and the oxidizing agent free composition may be applied simultaneously or in succession.

Customary, the oxidizing agent containing composition is evenly applied in a sufficient amount related to the amount of hair, usually in amounts of 30 to 200 g.

Oxidizing agents are for example persulfate or dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are
oxidizing agents to achieve lightened coloration, as described in WO 97/20545, especially p. 9, I. 5 to 9,
oxidizing agents in the form of permanent-wave fixing solution, as described in DE-A-19 713 698, especially p. 4, I. 52 to 55, and I. 60 and 61 or EP-A-1062940, especially p. 6, I. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% by weight the corresponding composition.

The oxidizing agents may be present in the dyeing compositions according to the invention preferably in an amount from 0.01% to 6%, especially from 0.01% to 3%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

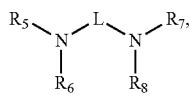

wherein
L is a propylene residue, which may be substituted with OH or $C_1$-$C_4$alkyl; and
$R_5$, $R_6$, $R_7$ and $R_8$ independently or dependently from each other are hydrogen; $C_1$-$C_4$alkyl; or hydroxy-($C_1$-$C_4$)alkyl.

The pH-value of the oxidizing agent containing composition is usually about 2 to 7, and in particular about 2 to 5.

One preferred method of applying formulations-comprising the dyes of formula (1a), (1b) and (1c) on the keratin-containing fiber, preferably the hair is by using a multi-compartment dyeing device or "kit" or any other multi-compartment packaging system, as described for example in WO 97/20545 on p. 4, I. 19 to I. 27.

Generally the hair is rinsed after treatment with the dyeing solution and/or permanent-wave solution.

A further preferred embodiment of the present invention relates to a method of dyeing hair with oxidative dyes, which comprises a. mixing at least one dye of formula (1a), (1b) and (1c) and optionally at least one coupler compound and at least one developer compound, and an oxidizing agent, which optionally contains at least one further dye, and
b. contacting the keratin-containing fibers with the mixture as prepared in step a.

For adjusting the pH-value organic or inorganic acids, as for example described in DE 199 59 479, col 3, I. 46 to I. 53 are suitable.

Furthermore, the present invention relates to a process of dyeing of keratin-containing fibers of the dyes of formula (1a), (1b) and (1c) with autooxidizable compounds and optionally further dyes.

The process comprises
a. mixing at least one autooxidizable compound and at least one developer compound and at least one dye of formula (1a), (1b) and (1c) and optionally further dyes, and
b. treating the keratin-containing fiber with the mixture prepared in step a.

Furthermore, the present invention relates to a process for dyeing keratin-containing fibers with the dyes of formula (1a), (1b) and (1c) and capped diazotised compounds, which comprises,
a. treating the keratin-containing fibers under alkaline conditions with at least one capped diazotised compound and a coupler compound, and optionally a developer compound ad optionally an oxidizing agent, and optionally in the presence of a further dye, and optionally with at least one dye of formula (1a), (1b) and (1c), and
b. adjusting the pH in the range of 6 to 2 by treatment with an acid, optionally in the presence of a further dye, and optionally at least one dye of formula (1a), (1b) and (1c),
with the proviso that at least in one step a. or b. at least one dye of formula (1a), (1b) and (1c) is present.

The capped diazotised compound and coupler compound and optionally the oxidizing agent and developer compound can be applied in any desired order successively or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

The alkaline dyeing compositions of step a. and the acid dyeing compositions of step b. are left on the fiber for 5 to 60 minutes at 15 to 45° C., in particular for 5 to 45 minutes at 20 to 30° C.

Furthermore, the present invention relates to a process for dyeing keratin-containing fibers with the dyes of formula (1a), (1b) and (1c) and at least one acid dye.

The following examples serve to illustrate the processes for dyeing without limiting the processes thereto. Unless specified otherwise, parts and percentages relate to weight. The amounts of dye specified are relative to the material being dyed.

PREPARATION EXAMPLES

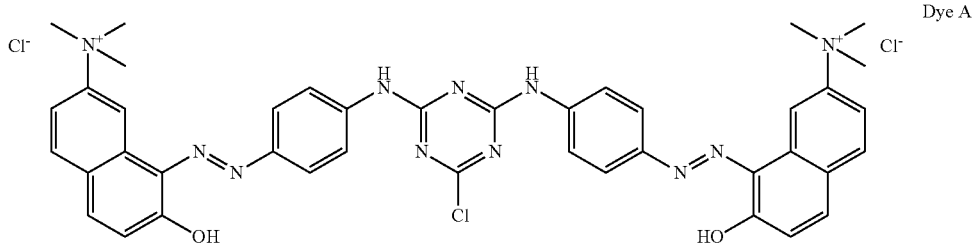

Dye A

The Dye A is prepared according to FR 2 873 369-A1

Example A1

0.102 g of polyethylenimine Aldrich CAS[29320-38-5], ref. 468533, Mn=423, (2.42 mmol per N) are dissolved in 2 ml of water. 0.2 g of Dye A (0.2 mmol) are added and the reaction mixture is stirred at 90° C. for 3 days.

After cooling the reaction mixture is diluted with water and washed 3 times with dichloromethane.

The aqueous phase is evaporated to dryness giving 0.25 g of a black powder.

Example A2

0.334 g of polyethylene imine Aldrich CAS[25987-06-8], ref. 408700, Mn=1800, 50% in water (3.98 mmol per N) is dissolved in 2 ml water.

0.2 g of Dye A (0.2 mmol) are added and the reaction mixture is stirred at 90° C. for 3 days.

After cooling the reaction mixture is diluted with water and washed 3 times with dichloromethane. The aqueous phase is evaporated to dryness giving 0.33 g of a black powder.

Further polymeric dyes are prepared in a similar way from the following dye building blocks described in patent EP 714954 and polyethyleneimine with an average $M_n$ of 600 (Adrich). The reaction conditions are given in Table 1.

The products are isolated from the reaction mixture by evaporation of the solvent.

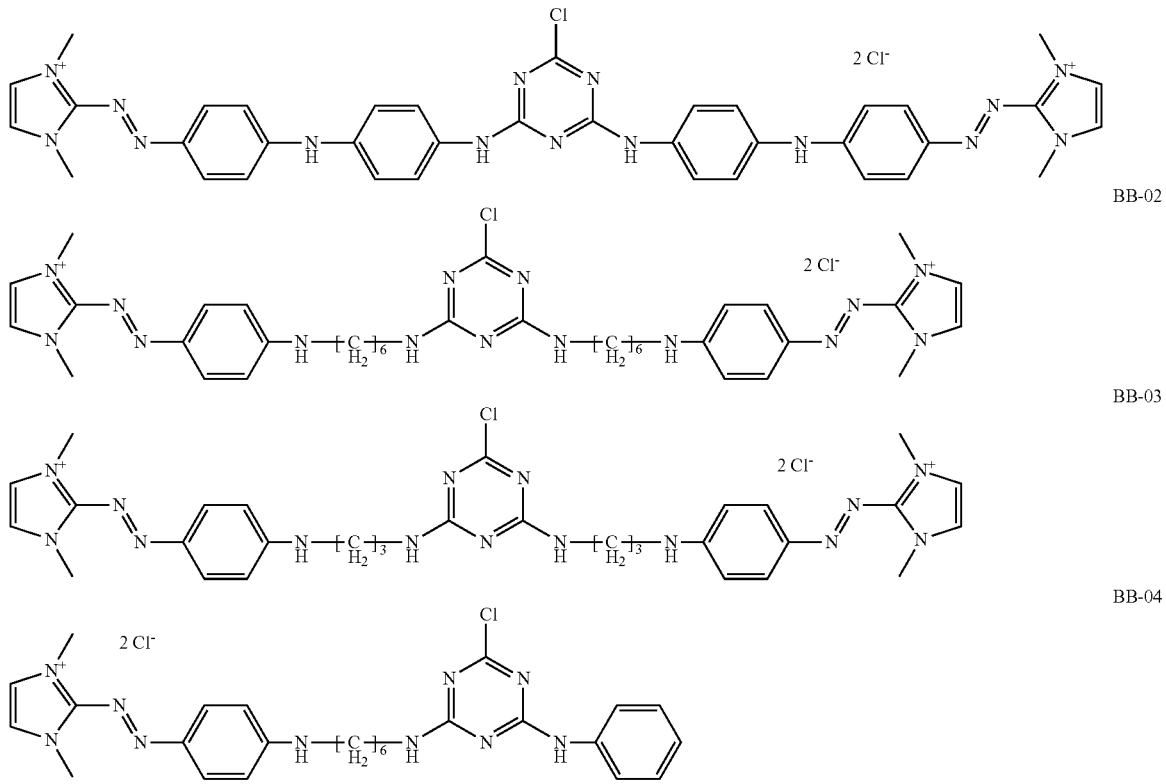

TABLE 1

Reaction conditions for the preparation of polymeric dyes from dye building blocks described iEP 0 757 083

| Ex. | Amount of Polymer | Used Building Block | Amount of Dye | Solvent | T [° C.] | Time | Yield | Product Color |
|---|---|---|---|---|---|---|---|---|
| A3 | 0.30 g | BB-01 | 1.0 g | deionized water 15 ml | 90° C. | 5 h | 1.1 g | violet |
| A4 | 0.29 g | BB-02 | 0.9 g | deionized water 15 ml | 90° C. | 5 h | 1.0 g | red |
| A5 | 0.32 g | BB-03 | 1.5 g | deionized water 15 ml | 70° C. | 5 h | 1.8 g | red |
| A6 | 0.30 g | BB-04 | 1.3 g | deionized water 30 ml | 80° C. | 5 h | 1.6 g | red |

Example A7

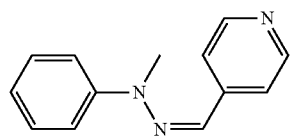

(107a)

Step 1: A mixture of 50.05 g of the hydrazon compound of formula (107) (described in WO 07/025889, ex. 6a) and 27.47 g 2-chloroethylammonium chloride in 300 ml n-butanol are stirred for 20 h at 115° C.

The reaction mixture is cooled to room temperature and the precipitated product is separated by filtration.

The filter cake is stirred under reflux in n-butanol, filtered off and dried to obtain 35.31 g of the compound of formula (107b).

LC-MS (ES+): m/z 255 (M+).

$^{13}C$ NMR (methanol-d4): δ [ppm] 153.542, 146.237, 143.574, 129.818, 125.715, 124.351, 122.814, 117.220, 56.509, 39.417, 34.721.

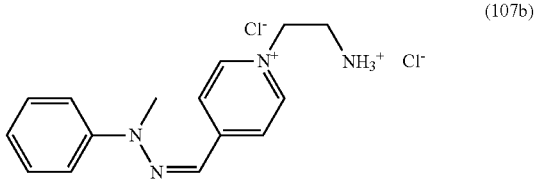

(107b)

Step 2: A solution of 2.5 g of the compound (107b) in 180 ml water is adjusted to pH 7.55 with sodium hydroxide.

Then a solution of 0.6 ml bromoacetylchloride in 2 ml acetone is added dropwise at −3° C. During the addition a pH of 7-8 is maintained by addition of sodium hydroxide.

When the pH remained constant 0.41 g polyethyleneimine (average $M_n$ 423; Adrich) is added and the reaction mixture is allowed to warm up to room temperature.

The reaction mixture is stirred for 4 days and the pH is kept at 7-8.

Then the solvent is evaporated, the residue is dissolved in methanol and 0.347 g conc. hydrochloric acid are added.

The solvent is evaporated to obtain 0.74 g of an orange oil, which is used for dyeing hair.

Example A8

Step 1: A mixture of 0.5 g of the compound (107a) and 2.42 ml 1,3-dibromopropane in 10 ml methylethylketone is stirred under reflux for 2 h.

Then the precipitate is collected by filtration and washed with methylethylketone.

The crude product is stirred in ethanol and the insoluble part is filtered off and discarded.

The solvent is completely removed from the filtrate by evaporation to obtain 0.65 g of a yellow oil of formula (108).

LC-MS (ES+): m/z 332, 334 (1:1).

$^{13}$C NMR (methanol-d4): δ[ppm] 154.620, 147.926, 144.955, 130.399, 126.383, 125.180, 123.441, 118.489, 59.773, 58.350, 35.633, 34.540, 29.406, 18.408.

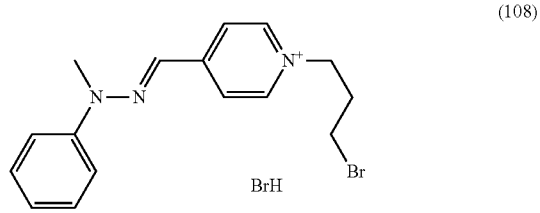

(108)

Step 2: A mixture of 1.855 g of poly-(2-dimethylaminoethyl)-acrylate (prepared by the method described in EP1275689 and DE19909767; average number of repeating units is 31) and 0.499 g of the compound (108) in 16 ml isopropanol is stirred for 18 h at 80° C.

Then 1.06 g of hydrochloric acid (37%) are added at room temperature.

The precipitate is isolated by filtration, washed with isopropanol and dried under reduced pressure to obtain 2.36 g of a yellow polymer that is used for dyeing hair.

$^1$H NMR (methanol-d4): δ[ppm] 8.913(br), 8.186(br), 7.731(br), 7.552(br), 7.417(br), 7.309(br), 7.232(br), 7.161(br), 4.725(br), 4.520(br), 3.987(br), 3.853(br), 3.608(br), 3.396(br), 3.359(br), 3.033(br), 2.662(br), 2.158(br), 1.938(br), 1.757(br).

Example A9

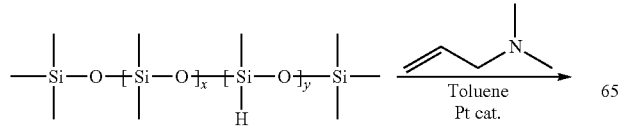

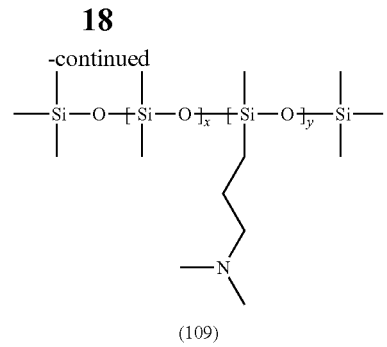

(109)

Gelest HMS 301;
MW 1900-2000;
25-30 Mol % SiH

To a solution of 10 ml methylhydrosiloxane-dimethylsiloxane copolymer [68037-59-2] (Gelest HMS 301; MW1900-2000, 25-30 mol % SiH, d=0.98; 40 mmol eq.) in 35 ml toluene are added 5.68 ml of N,N-dimethylallylamine (48 mmol) and 200 μl of platinum (0)-1,3-divinyl-1,1,3,3-tetramethyldisiloxane complexed in xylene [68478-92-2].

The reaction mixture is agitated for 2 days at 55° C. and then evaporated to dryness to give 14.647 g polymer of formula (109).

Example A10

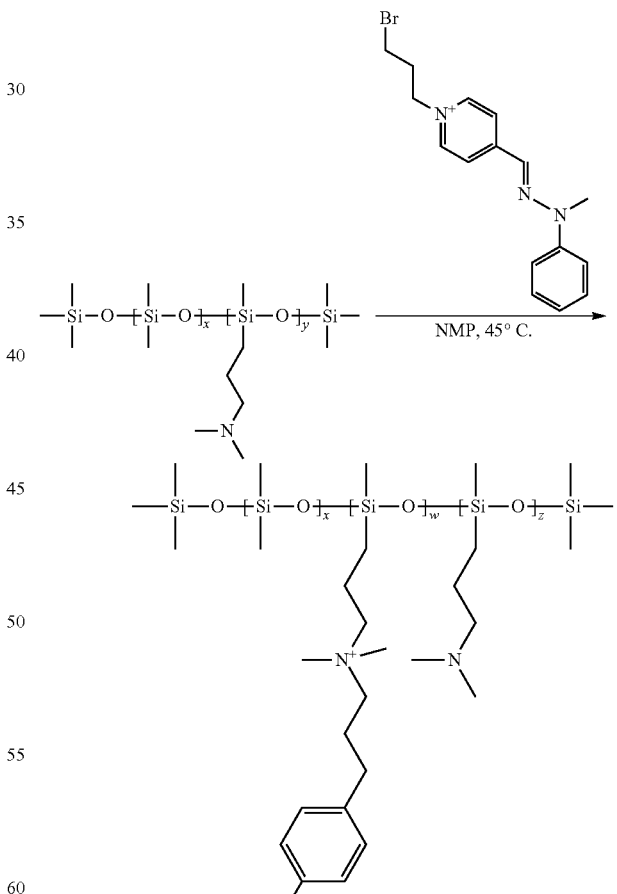

(110)

1650 mg of polysiloxane A-9 (5 meq. N) are taken in 5 ml NMP and reacted with 0.518 g of the dye of formula (108) (1.2 mmol) for 14 days at 45° C.

The evolution of the reaction is monitored by TLC. T

The NMP solution is used without further treatment for coloration test.

Example A11

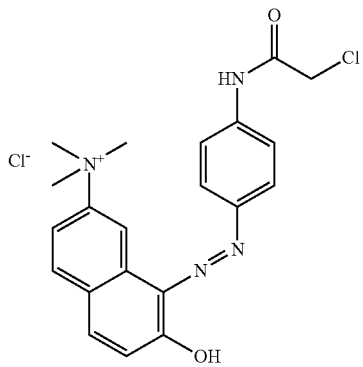

(111)

A suspension of 1.14 g of basic brown 16 (4 mmol) in 1 ml acetonile is cooled to 0° C. and 0.687 g chloroacetylchloride (6 mmol) are added dropwise over 10 min to the reaction mixture. 12 ml of dichloromethane are then added to improve the solubility.

After stirring at room temperature for 19 h an additional 0.92 g of chloroacetylchloride (8 mmol) are added and the reaction mixture was heated at 40° C. for 1.5 h.

After cooling the mixture is diluted with 40 ml acetone.

A solid precipitated, it is filtered off, washed with acetone and dried yielding 1.24 g (71%) of a pale brown powder of formula (111).

MS (ES+): m/z 397. UV/VIS (methanol): λmax 475 nm. 1H NMR (dmso-d6): δ[ppm] 15.25 (s, 1H), 11.0 (s, 1H), 8.9 (s, 1H), 8.2-8.0 (m, 5H), 7.85 (d, 2H), 7.25 (d, 2H), 4.3 (s, 2H), 3.7 (s, 9H)

Example A12

0.150 g of compound of formula (111) (0.346 mmol), 0.037 g triethylamine (0.36 mmol) and 0.011 g potassium iodide (0.069 mmol) are added to a suspension of 0.045 g Polyamine B (Akzo Nobel) (1.05 meq.N) in 3 ml acetonitrile/methanol (1/2).

The reaction mixture is stirred at 40° C. for 30 h and at 55° C. for 23 h.

After cooling the reaction mixture is diluted with 7.5 ml ethylacetate and washed twice with ethylacetate.

The solid is taken in 12 ml chloroform and 12 ml dichloromethane, then filtered again, washed with dichloromethane and dried under vacuum to give after drying 0.1 g (67%) of a pale brown powder.

1H NMR (D$_2$O): δ[ppm] 8.5-5.7 (br, 9H), 4.2-2.5 (br 26H)

Example A13

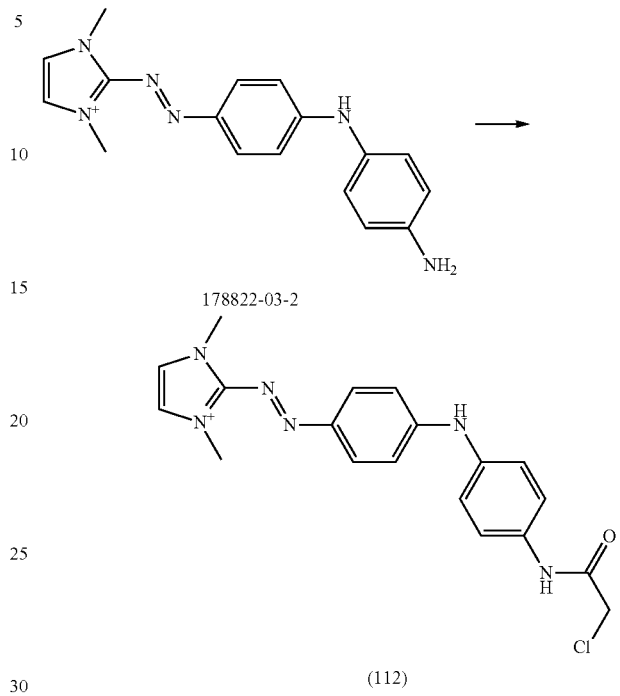

178822-03-2

(112)

0.206 g of [178822-03-2] (0.6 mmol), prepared as described in EP 1 219683 are solubilised in 2 ml of acetonitrile.

A solution of 0.075 g chloroacetylchloride (0.66 mmol) is added dropwise and the reaction mixture is stirred at room temperature for 20 h and then evaporated to dryness.

The solid is solubilised in a mixture of ethylacetate, dichloromethane and acetonitrile (5/15/5 vol) and toluene (75 vol) are added to precipitate the product which is filtered and washed with toluene.

After drying under vacuum, 51 g of a dark violet powder are obtained (99% yield).

MS (ES+): m/z 383. 1H NMR (dmso-d6): δ[ppm] 10.6 (s, 1H), 9.95 (s, 1H), 7.9 (s, 2H), 7.75 (s, 2H), 7.65 (s, 2H), 7.3 (s, 2H), 7.15 (s, 2H), 4.25 (s, 2H), 3.95 (s, 6H)

Example A14

0.047 g Polyamine B (Akzo Nobel) (1.08 mmol N) and 0.15 g of the chloride of formula (112) (0.358 mmol) are reacted in 2 ml methanol at 55° C. over 30 h.

After cooling acetone is added and the polymer precipitate. It is filtered and washed with acetone giving after drying 120 mg of a dark violet powder (66%).

1H NMR (D$_2$O): δ[ppm] 8.2-6.5 (br, 10H), 4.2-2 (br, 12H)

B. Application Examples

For the application examples the following hair types are used:

1 blonde hair tress (VIRGIN White Hair from IMHAIR Ltd., via G. Verga 8, 90134 Palermo (Italy)), 1 middle blonde hair tress (UNA-Europ. nature hair, Color middle blonde from Fischbach & Miller, Postfach 1163, 88461 Laupheim, Germany), 1 bleached hair tress (UNA-Europ. nature hair, Color white bleached blonde from Fischbach & Miller, Postfach 1163, 88461 Laupheim, Germany).

Wash Fastness

To determine the wash fastness two sets of hair tresses are dyed under the same conditions. One set of the dyed tresses is washed with a commercial shampoo (GOLDWELL definition Color & Highlights, color-conditioner shampoo) using approx. 0.5 g shampoo for each tress under tap water (water temperature: 37° C.+/−1° C.; flow rate 5-6 l/min).

Finally the tresses are rinsed under tap water, pressed out with a paper towel, combed and dried with a hair dryer or at room temperature. This procedure was repeated 10 times.

Then the color loss of the set of washed tresses relative to the set of unwashed tresses is evaluated using the Grey Scale according to: Industrial Organic Pigments by Herbst&Hunger, 2nd ed., p. 61, Nr 10: DIN 54 001-8-1982, "Herstellung and Bewertung der Änderung der Farbe", ISO 105-A02-1993.

| Example | Dye | Hair Type | Color | Intensity | Brilliance | Wash-fastness Grey scale |
|---|---|---|---|---|---|---|
| B1 | A1 | blond | brown | moderate | moderate | 4-5 |
|  |  | middle blond | brown | moderate | moderate | 5 |
|  |  | bleached | brown | moderate | moderate | 4 |
| B2 | A2 | blond | brown | moderate | moderate | 4-5 |
|  |  | middle blond | brown | moderate | moderate | 5 |
|  |  | Bleached | brown | moderate | moderate | 4 |
| B3 | A3 | blond | violet | moderate | moderate | 2-3 |
|  |  | middle blond | violet | moderate | moderate | 3-4 |
|  |  | bleached | violet | good | good | 3 |
| B4 | A7 | blond | yellow | good | good | 3-4 |
|  |  | middle blond | yellow | good | good | 4-5 |
|  |  | bleached | yellow | good | good | 3-4 |
| B5 | A8 | blond | yellow | good | good | 3-4 |
|  |  | middle blond | yellow | good | good | 4-5 |
|  |  | bleached | yellow | good | good | 4 |
| B6 | A10 | blond | yellow | good | good | 3-4 |
|  |  | middle blond | yellow | good | good | 4 |
|  |  | bleached | yellow | good | good | 4 |
| B7 | A12 | blond | orange | good | good | 2-3 |
|  |  | middle blond | orange | good | good | 4 |
|  |  | bleached | orange | good | good | 3 |
| B8 | A14 | blond | violet | good | good | 4 |
|  |  | middle blond | violet | good | good | 4 |
|  |  | bleached | violet | good | good | 4 |

The invention claimed is:

1. Polymeric dye of formula

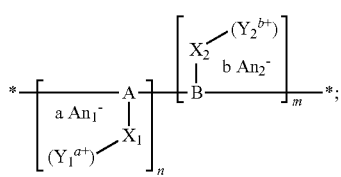

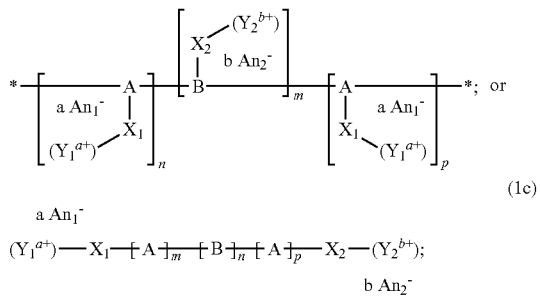

wherein

A and B, independently from each other represent a polymer backbone;

$X_1$ and $X_2$ independently from each other are a linkage group selected from —$C_1$-$C_{30}$alkylene- or —$C_2$-$C_{12}$alkenylene-, which is interrupted and/or terminated at one or both ends by one or more than one —S—, —N—, —N=, —N($R_5$)—, —S(O)—, —$SO_2$—, —($CH_2CH_2$—O$)_{1-5}$—, —($CH_2CH_2CH_2$—O$)_{1-5}$—, —C(O)—, —C(O)O—, —OCO—,

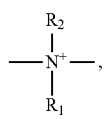

—CON($R_1$)—, —C($NR_1R_2$)$_2$—, —($R_1$)NC(O)—, —C(S)$R_1$—; or an optionally substituted, saturated or unsaturated, fused or non-fused aromatic or nonaromatic (heterocyclic) bivalent radical optionally comprising at least one heteroatom; a saturated or unsaturated, fused or non-fused aromatic or nonaromatic bivalent radical comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or halogen;

$R_1$ and $R_2$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

$Y_1$ and $Y_2$ independently from each other are a residue of an organic dye; or hydrogen; wherein at least one of $Y_1$ and $Y_2$ is a residue of an organic dye;

$An_1$, $An_2$ and $An_3$, independently from each other are an anion;

a and b independently from each other are a number from 1 to 3;

m is a number from 0 to 5000;

n is a number from 0 to 5000; and p is a number from 1 to 5000;

wherein the sum of m+n+p≧3.

2. Dye according to claim 1, wherein $X_1$ and $X_2$ independently from each other are a bivalent radical of formula -(T)$_t$(Z)—,     (1a) wherein T is —$C_1$-$C_{12}$alkylene; —$C_2$-$C_{12}$alkenylene-; —C(O)—; —($CH_2CH_2$—O$)_{1-5}$—; —($CH_2CH_2CH_2$—O$)_{1-5}$—; —C(O)O—; —OC(O)—; —N($R_1$)—; —CON($R_1$)—; —($R_1$)NC(O)—; —O—; —S—; —S(O)—; —S(O)$_2$—; —S(O)$_2$N($R_1$)—; or —$N^+(R_1)(R_2)$—;

Z is a biradical of formula

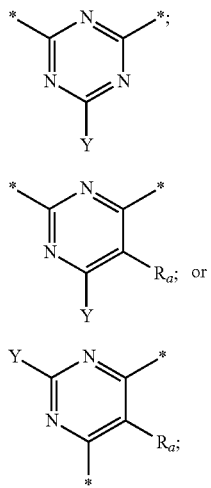

$R_1$ and $R_2$ independently from each other are hydrogen; $C_1$-$C_6$alkyl; $C_1$-$C_6$alkoxy; $C_1$-$C_6$-alkylamino; $C_6$-$C_{10}$aryloxy; or $C_6$-$C_{10}$arylamino;

$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; $SO_2R_5$; chlorine; or fluorine;

Y is $R_a$; $Y_1^{a+}$; or $Y_2^{b+}$; wherein $Y_1$ and $Y_2$ are defined as in claim 1;

a and b independently from each other are 1, 2 or 3; and t is 0 or 1.

3. Dye according to claim 1, wherein $Y_1$ and $Y_2$ independently from each other are selected from the group of anthraquinone, acridine, azo, azamethine, hydrazomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, quinoneimine, quinacridone, quinophtalone, styryl, stilbene, xanthene, thiazine and thioxanthene dyes.

4. Dye according to claim 1, wherein $Y_1$ and $Y_2$ independently from each other are selected from azo, azomethine, hydrazomethine, anthraquinone, merocyanine, methine and styryl dyes.

5. Dye according to claim 1, wherein $Y_1$ and $Y_2$ have the same meaning.

6. Dye according to claim 1, wherein

A and B, independently from each other are selected from polyethylenimine, polypropyleneimine, polyvinylamine; polyvinylimine; polysiloxane; polystyrene, polyvinylimidazol, polyvinylpyridine, polyDADMAC, polyvinylalcohol, polyacrylate, polymethacrylate; polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; polysaccharide, starch, cellulose, lignin; and copolymers and blends of the mentioned polymers.

7. Dye according to claim 1, wherein both the polymer backbone (A and B) and residue of an organic dye ($Y_1$ and $Y_2$) have a functional group selected from the electophilic group selected from halide, tosylate, mesylate, methoxy, acid chloride, sulfonyl chloride, epoxides, anhydride; or a nucleophilic group selected from amine, hydroxyl and thiol.

8. Dye according to claim 1, wherein the molecular weight of the polymeric dye is from 400 to 50000.

9. Dye according to claim 1, which corresponds to formula

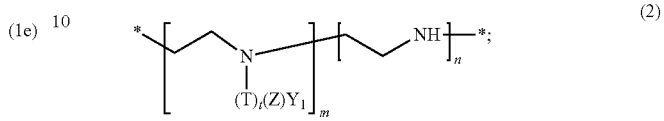

wherein

T is —$C_1$-$C_{12}$alkylene; —$C_2$-$C_{12}$alkenylene-; —C(O)—; —(CH$_2$CH$_2$—O)$_{1-5}$—; —(CH$_2$CH$_2$CH$_2$—O)$_{1-5}$—; —C(O)O—; —OC(O)—; —N(R$_1$)—; —CON(R$_1$)—; —(R$_1$)NC(O)—; —O—; —S—; —S(O)—; —S(O)$_2$—; —S(O)$_2$N(R$_1$)—; or —N$^+$(R$_1$)(R$_2$)—;

Z is a biradical of formula (1d)

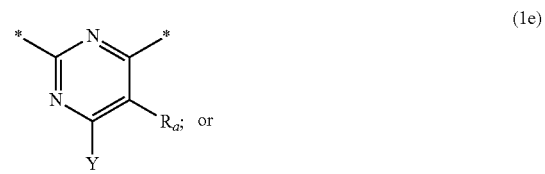

$R_1$ and $R_2$ independently from each other are hydrogen; $C_1$-$C_6$alkyl; $C_1$-$C_6$alkoxy; $C_1$-$C_6$-alkylamino; $C_6$-$C_{10}$aryloxy; or $C_6$-$C_{10}$arylamino;

$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; $SO_2R_5$; chlorine; or fluorine;

Y is $R_a$; $Y_1^{a+}$; or $Y_2^{b+}$;

a and b independently from each other are 1, 2 or 3; and t is 0 or 1; and m and n are defined as in claim 1.

10. Dye according to claim 9, which corresponds to formula

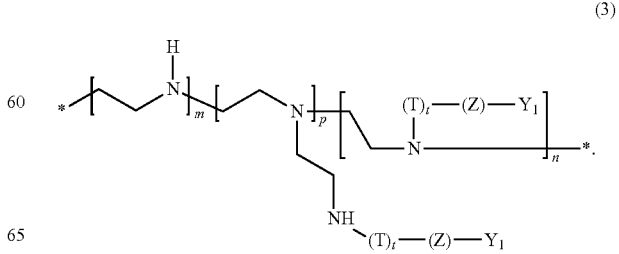

11. Dye according to claim 1, which corresponds to formula

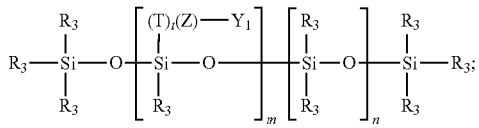 (4)

wherein
$R_3$ is $C_1$-$C_5$alkyl;
T is —$C_1$-$C_{12}$alkylene; —$C_2$-$C_{12}$alkenylene; —C(O)—; —(CH$_2$CH$_2$—O)$_{1-5}$—; —(CH$_2$CH$_2$CH$_2$—O)$_{1-5}$—; —C(O)O—; —OC(O)—; —N(R$_1$)—; —CON(R$_1$)—; —(R$_1$)NC(O)—; —O—; —S—; —S(O)—; —S(O)$_2$—; —S(O)$_2$N(R$_1$)—; or —N$^+$(R$_1$)(R$_2$)—;
Z is a biradical of formula

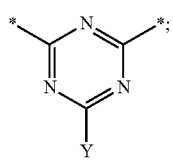 (1d)

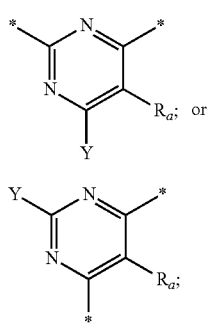 (1e)

(1f)

$R_1$ and $R_2$ independently from each other are hydrogen; $C_1$-$C_6$alkyl; $C_1$-$C_6$alkoxy; $C_1$-$C_6$-alkylamino; $C_6$-$C_{10}$aryloxy; or $C_6$-$C_{10}$arylamino;
$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; SO$_2$R$_5$; chlorine; or fluorine;
Y is $R_a$; $Y_1^{a+}$; or $Y_2^{b+}$;
a and b independently from each other are 1, 2 or 3; and
t is 0 or 1.

12. Dye according to claim 1, which corresponds to formula

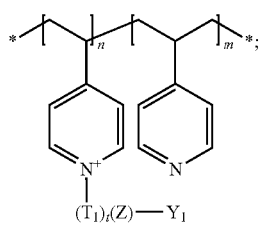 (5)

wherein
T is —$C_1$-$C_{12}$alkylene; —$C_2$-$C_{12}$alkenylene-; —C(O)—; —(CH$_2$CH$_2$—O)$_{1-5}$—; —(CH$_2$CH$_2$CH$_2$—O)$_{1-5}$—; —C(O)O—; —OC(O)—; —N(R$_1$)—; —CON(R$_1$)—; —(R$_1$)NC(O)—; —O—; —S—; —S(O)—; —S(O)$_2$—; —S(O)$_2$N(R$_1$)—; or —N$^+$(R$_1$)(R$_2$)—;
Z is a biradical of formula

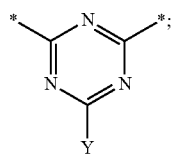 (1d)

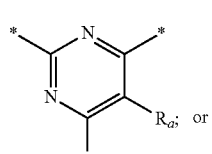 (1e)

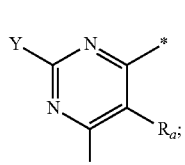 (1f)

$R_1$ and $R_2$ independently from each other are hydrogen; $C_1$-$C_6$alkyl; $C_1$-$C_6$alkoxy; $C_1$-$C_6$-alkylamino; $C_6$-$C_{10}$aryloxy; or $C_6$-$C_{10}$arylamino;
$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; SO$_2$R$_5$; chlorine; or fluorine;
Y is $R_a$; $Y_1^{a+}$; or $Y_2^{b+}$;
a and b independently from each other are 1, 2 or 3; and
t is 0 or 1.

13. Dye according to claim 1, which corresponds to formula

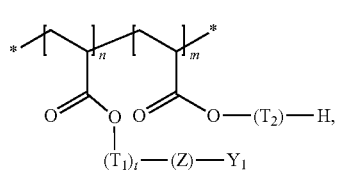 (6)

wherein
$T_1$ and $T_2$, independently from each other are —$C_1$-$C_{12}$alkylene; —$C_2$-$C_{12}$alkenylene-; —C(O)—; —(CH$_2$CH$_2$—O)$_{1-5}$—; —(CH$_2$CH$_2$CH$_2$—O)$_{1-5}$—; —C(O)O—; —OC(O)—; —N(R$_1$)—; —CON(R$_1$)—; —(R$_1$)NC(O)—; —O—; —S—; —S(O)—; —S(O)$_2$—; —S(O)$_2$N(R$_1$)—; or —N$^+$(R$_1$)(R$_2$)—; and
T is —$C_1$-$C_{12}$alkylene; —$C_2$-$C_{12}$alkenylene-; —C(O)—; —(CH$_2$CH$_2$—O)$_{1-5}$—; —(CH$_2$CH$_2$CH$_2$—O)$_{1-5}$—; —C(O)O—; —OC(O)—; —N(R$_1$)—; —CON(R$_1$)—; —(R$_1$)NC(O)—; —O—; —S—; —S(O)—; —S(O)$_2$—; —S(O)$_2$N(R$_1$)—; or —N$^+$(R$_1$)(R$_2$)—;

Z is a biradical of formula

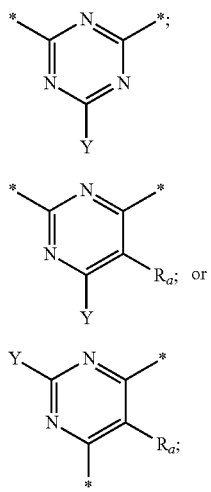

(1d)

(1e)

(1f)

$R_1$ and $R_2$ independently from each other are hydrogen; $C_1$-$C_6$alkyl; $C_1$-$C_6$alkoxy; $C_1$-$C_6$-alkylamino; $C_6$-$C_{10}$aryloxy; or $C_6$-$C_{10}$arylamino;

$R_a$ is hydrogen; $C_1$-$C_6$alkyl; $C_1$-$C_6$-alkoxy; $C_1$-$C_6$-alkylamino; $C_6$-$C_{10}$aryloxy; $C_6$-$C_{10}$-arylamino; $SO_2R_5$; chlorine; or fluorine;

Y is $R_a$; $Y_1^{a+}$; or $Y_2^{b+}$;

a and b independently from each other are 1, 2 or 3; and t is 0 or 1.

14. A composition comprising at least one dye of formula (1a), (1b) or (1c) as defined in claim 1.

15. A composition according to claim 14 comprising in addition at least one single further direct dye and/or an oxidative agent.

16. A composition according to claim 14 in the form of a shampoo, a conditioner, a gel or an emulsion.

17. A method of dyeing organic material, which comprises treating the organic material with at least one dye of formula (1a), (1b) or (1c) according to claim 1.

18. A method according to claim 17, which comprises treating the organic material with at least one dye of formula (1a), (1b) or (1c) and an oxidative agent and, optionally, a further direct dye.

19. A method according to claim 17, which comprises treating the organic material with at least one compound of formula (1a), (1b) or (1c ) and at least one single oxidative dye, or treating the organic material with a dye of formula (1a), (1b) or (1c) and at least one single oxidative dye and an oxidative agent.

20. A method according to claim 17 wherein the organic material is human hair.

* * * * *